United States Patent [19]
Hahn et al.

[11] Patent Number: 5,306,267
[45] Date of Patent: Apr. 26, 1994

[54] REUSABLE, ALL-IN-ONE, MULTI-LAYERED DIAPER WITH WICKING ACTION, MOISTURE RETENTION, AND METHODS FOR MAKING AND USING SAME

[75] Inventors: Janice L. Hahn; Edwin K. Hahn; Melody Taylor, all of Idaho Falls, Id.

[73] Assignee: J & E Enterprise, Idaho Falls, Id.

[21] Appl. No.: 817,149

[22] Filed: Jan. 6, 1992

[51] Int. Cl.⁵ .................. A61F 13/15; A61F 13/20
[52] U.S. Cl. .................. 604/378; 604/358; 604/371; 604/374; 604/385.1
[58] Field of Search .............. 604/358, 367, 371, 372, 604/374, 378, 385.1; 428/284

[56] References Cited

U.S. PATENT DOCUMENTS

| | | | |
|---|---|---|---|
| Re. 30,972 | 6/1982 | Kyle et al. | 428/219 |
| 2,682,873 | 7/1954 | Evans et al. | 604/378 |
| 3,719,189 | 3/1973 | Sherman | 128/287 |
| 3,720,212 | 3/1973 | Kaupin | 604/378 |
| 4,037,602 | 7/1977 | Hawthorne | 604/385.1 |
| 4,128,686 | 12/1978 | Kyle et al. | 428/219 |
| 4,381,781 | 5/1983 | Sciaraffa et al. | 604/372 |
| 4,425,126 | 1/1984 | Butterworth et al. | 604/366 |
| 4,480,000 | 10/1984 | Watanabe et al. | 428/284 |
| 4,551,144 | 11/1985 | Graber | 604/378 |
| 4,573,987 | 3/1986 | Lamb, Jr. | 604/378 |
| 4,675,014 | 6/1987 | Sustmann et al. | 604/375 |
| 4,718,899 | 1/1988 | Itoh et al. | 604/368 |
| 4,772,281 | 9/1988 | Armstead | 604/383 |
| 4,801,298 | 1/1989 | Sorenson et al. | 604/384 |
| 4,927,685 | 5/1990 | Marshall et al. | 428/74 |
| 4,943,286 | 7/1990 | Armstead | 604/358 |
| 4,978,345 | 12/1990 | Holliday et al. | 604/384 |
| 5,085,653 | 2/1992 | Levy | 604/383 |

*Primary Examiner*—Randall L. Green
*Assistant Examiner*—A. Zuttarelli
*Attorney, Agent, or Firm*—Workman, Nydegger & Jensen

[57] ABSTRACT

Novel apparatus and methods for a reusable, multi-layered diaper are disclosed. The diaper offers maximum health protection and ecological sensibility, with an ideal balance of comfort, cost and absorbency utilizing a unique multi-layered construction. The multi-layered construction comprises a first layer contacting a body, the first layer being a polyester wicking fabric. The multi-layered construction also comprises a middle layer associated with the first layer. The middle layer being significantly absorbent and characterized by the presence of viscose fibers to increase the absorbency of at least one middle layer. The multi-layered construction further comprises an outer layer associated with at least one middle layer. The outer layer being impermeable to liquids such that the diaper is waterproof. The present invention also comprises methods for making the reusable, multilayered diaper.

25 Claims, 3 Drawing Sheets

REUSABLE, ALL-IN-ONE, MULTI-LAYERED DIAPER WITH WICKING ACTION, MOISTURE RETENTION, AND METHODS FOR MAKING AND USING SAME

BACKGROUND

The Field of the Invention

The present invention relates to apparatus and methods for a reusable, multi-layered diaper with wicking action and moisture retention. In particular, the preferred embodiment of the invention relates to apparatus and methods for a reusable, multi-layered diaper which employs a polyester wicking fabric to keep moisture away from the skin of an infant, and an ultra absorbent material to contain a previously collected amount of the wicked away moisture from the body of the infant.

The Background Art

Diapers have been known almost since the beginning of mankind. In their traditional configuration, a diaper consists generally of a rectangular-shaped piece of absorbent cloth or fabric. The fabric is generally folded into a triangular configuration which is adapted to be fitted about the lower abdominal region of an infant. In a conventional construction, the corners of the triangular-shaped folded fabric are joined one to another by means of various types of adhesive or connecting means. One widely used means is that of a safety pin. Of more recent vintage, is the use of adhesive-backed strips which are adapted to adhere, or connect to the fabric of the diaper. Also in use are various types of hook and pile fasteners. These latter type attachments are exemplified by those made commercially available by the Velcro ® Corporation of New York, N.Y., and traditionally sold under the trade designation "Velcro ®."

Ecological concerns are becoming increasingly important in different aspects of many individuals' lifestyles. It is now apparent that even the most commonplace practice can have significant ecological ramifications. Nowhere is this more apparent than in the use of disposable diapers for infants.

Disposable diapers typically include a large degree of modern synthetic materials which are not easily biodegradable. Examples of such synthetic materials include different types of plastics such as nylons, polyesters, polybutals, and polyethylenes. The degradation of such plastics can take decades to centuries.

It can be expected that in 1991, approximately eighteen billion disposable diapers will be sold in the United States. The world market can reasonably be expected to be significantly larger in light of the small proportion of children residing in the United States when compared to the number of children in the entire world. Thus, this large amount of diapers sold, which comprises a large amount of modern synthetic materials, will significantly affect the biological environment.

Moreover, the use of disposable diapers can also affect the environment in other ways. Intestinal and polio viruses can survive for long periods of time in disposable diapers, thereby contaminating landfills and water supplies. Furthermore, disposable diapers can provide an active culture site for odor-causing microorganisms such that their disposal creates an area most humans must avoid for health reasons.

As a consequence of the ecological and health concerns raised by disposable diapers, the demand for reusable diapers has increased. Reusable diapers can be characterized by the fact that the diaper will not disassemble or erode after being washed. Generally, such a construction involves the use of cotton flannel, polybutal and dacron batting.

Although reusable diapers solve the ecological and health concerns raised by disposable diapers, the use of reusable diapers has not solved all the problems associated with diapers. Foremost among these problems is that currently used reusable diapers are not effective in absorbing many times their weight in liquid. Today's reusable diapers only absorb a limited amount of liquid and, therefore, rash-causing moisture is not drawn away from the baby's skin.

In addition, currently known reusable diapers are not effective even if only a small amount of liquid is present. The limited absorbent capacity of the currently known reusable diapers will be able to draw away a limited amount of liquid, but will not retard moisture from flowing back to a baby's skin. Because the absorbed moisture is not retarded from flowing back to a baby's skin, the baby's skin is still susceptible to the rash-causing moisture.

In light of the foregoing, it is clear that all of the problems presented in the reusable diaper area have not been solved. A market is available for a reusable diaper which could solve these additional problems not remedied by currently known reusable diapers. A need, therefore, exists in the art for a diaper which is reusable and provides an ecologically sensible alternative to disposable diapers.

Also, a need exists in the art for a diaper which will absorb many times its weight in liquids.

Additionally, a need exists in the art for a diaper which will absorb many times its weight while holding rash-causing moisture away from a baby's skin.

Further, a need exists in the art for a diaper containing a layer of material that retards moisture from flowing back to a baby's skin.

BRIEF SUMMARY AND OBJECTS OF THE INVENTION

The present invention seeks to resolve problems incident to the diapering of infants. More specifically, the apparatus and methods of this invention constitute an important advance in the diaper art by providing a reusable, multi-layered diaper which employs a polyester wicking fabric to keep moisture away from the body of an infant, and an ultra absorbent material to contain the moisture wicked away from the body of the infant.

One object of the present invention is to provide an apparatus and methods for a diaper which is reusable and provides for an ecologically sensible alternative to disposable diapers.

Also, it is an object of the present invention to provide an apparatus and methods for a diaper which will absorb many times its weight in liquids.

Additionally, it is an object of the present invention to provide an apparatus and methods for a diaper which will absorb many times its weight while holding rash-causing moisture away from a baby's skin.

Still another object of the present invention is to provide an apparatus and methods for a diaper containing a layer of material that retards moisture from flowing back to a baby's skin.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a multi-layered diaper is provided offering maximum health protection with an ideal balance of comfort, cost, and absorbency. The diaper is reusable and, therefore, ecologically sound. The objects are achieved by the unique multi-layered construction of the diaper.

A first layer employed in the multi-layered construction of the diaper is positioned such that it contacts the body of the infant. The first layer is comprised of a polyester wicking fabric. A currently preferred polyester wicking fabric is marketed under the trade name of COOL MAX ® by the DuPont Corporation, although other manufacturers may distribute a similar, usable material. The polyester of this wicking fiber comprises a four-channel fiber featuring a unique structure with 20% more surface area than ordinary fibers.

The reusable, multi-layered diaper further comprises at least one middle layer associated with the first layer. The middle layer(s) is characterized by the presence of viscose fibers to increase the absorbency of the middle layer(s). A preferred viscose-containing middle layer is marketed under the trade name of VISCOSE ® by HUDCO, located in Hayward, California, although other manufacturers may distribute a similar usable material. The composition of this layer is primarily viscose fibers which increases the absorbency of the composition.

The reusable, multi-layered diaper further comprises an outer layer associated with the at least one middle layer. The outer layer being impermeable to liquids such that the diaper is water-proof. A preferred outer layer is comprised of nylon.

In addition to the unique multi-layered nature of the diaper, other features are presented such that the diaper is designed to better fit an infant. The use of Velcro ®-type fasteners eliminate the need for clumsy, dangerous pins and adjust for perfect fit as a baby grows. Also, the diaper can be more "T"-shaped to eliminate excess bulk across the hip associated area of the diaper to better conform to a baby's shape.

The present invention also comprises methods for manufacturing the reusable, multi-layered diaper. The methods for manufacturing the reusable, multi-layered diaper comprises the steps of providing a first layer that contacts the body of an individual, the first layer being a polyester wicking fabric.

A further step is contacting at least one middle layer with the first layer. The at least one middle layer being characterized by the presence of viscose fibers to increase the absorbency of the at least one middle layer. This enables a greater amount of liquid to be maintained in the at least one middle layer, away from the body of an infant.

A still further step comprises positioning an outer layer in association with the at least one middle layer. The outer layer being impermeable to liquids such that the diaper is water-proof. This prevents the spread of absorbed liquids to areas about the diaper, such as outer clothing or other surface a baby wearing a diaper may pass against.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which:

FIG. 3 illustrates the multi-layered nature of the diaper disclosed in the present invention.

FIG. 4 illustrates an alternate multi-layered diaper wherein cotton-containing layers are placed in association with one side of the middle layer.

FIG. 5 illustrates an alternate multi-layered diaper wherein a cotton-containing layer is placed in association with both sides of the middle layer.

DETAILED DESCRIPTION OF THE PREFERRED EMBODIMENTS

Figure 1:
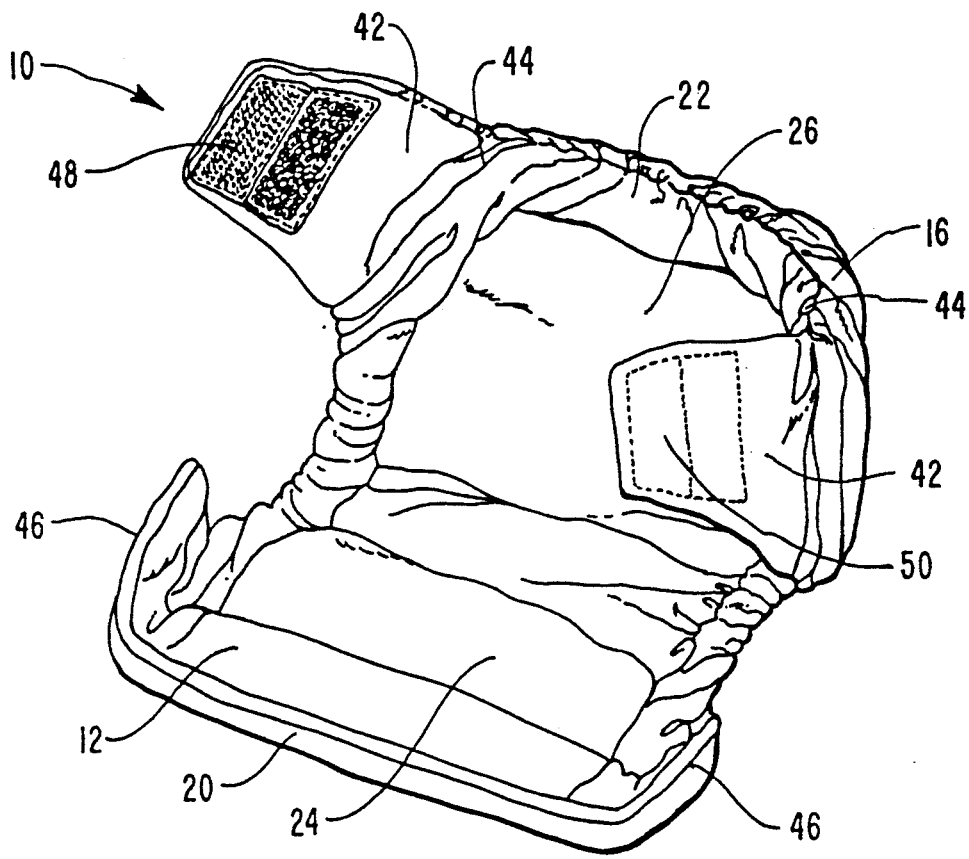
FIG. 1 is a perspective view of the present invention as it would appear before use on an infant.

The present invention can be best understood by reference to the drawings, wherein like parts are designated with like numerals throughout. The present invention as it pertains to a diaper 10 can be understood with reference to FIG. 1. FIG. 1 illustrates the diaper disclosed in the present invention in one of its embodiments.

Diaper 10 defines three main components, a front panel 12, a middle panel 14, and a back panel 16. More specifically, front panel 12 includes a sheet of a polyester wicking fabric, as detailed below, for drawing moisture away from the surface it contacts, such as the buttocks of an infant. Middle panel 14 includes a sheet of a viscose-fiber-containing material, as detailed below for containing a large amount of liquid drawn away by first panel 12, the liquid is drawn away due to the absorbency of middle panel 14. Back panel 16 includes a sheet of water-proof nylon, as detailed below for providing an impermeable barrier between the previously discussed panels and any surfaces with which these panels may come in contact. Diaper 10 includes other features which will be discussed in greater depth at a later point.

Figure 2:
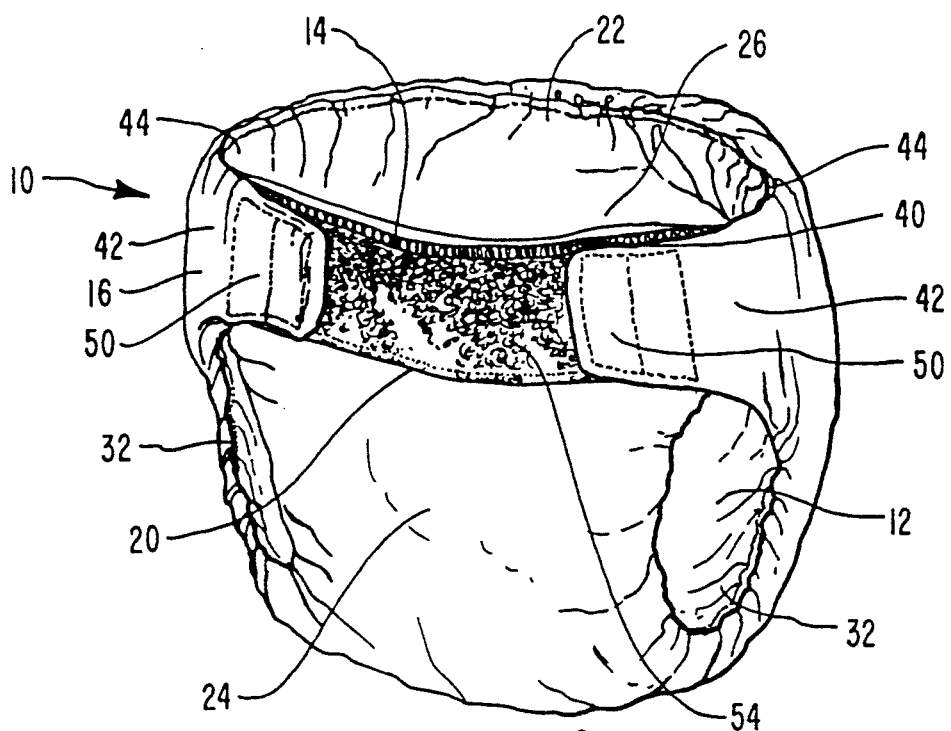
FIG. 2 is a perspective view of the present invention as it would appear during use on an infant.

FIG. 2 is a perspective view of diaper 10 as it would appear during use on an infant. As it will be discussed in greater depth at a future point, diaper 10 is snugly configured about the waist area and legs of an infant such that leakage is prevented therefrom. Diaper 10 may be constructed in various sizes to snugly fit about the waist area and legs of all individuals known to those in the art.

Figure 3:
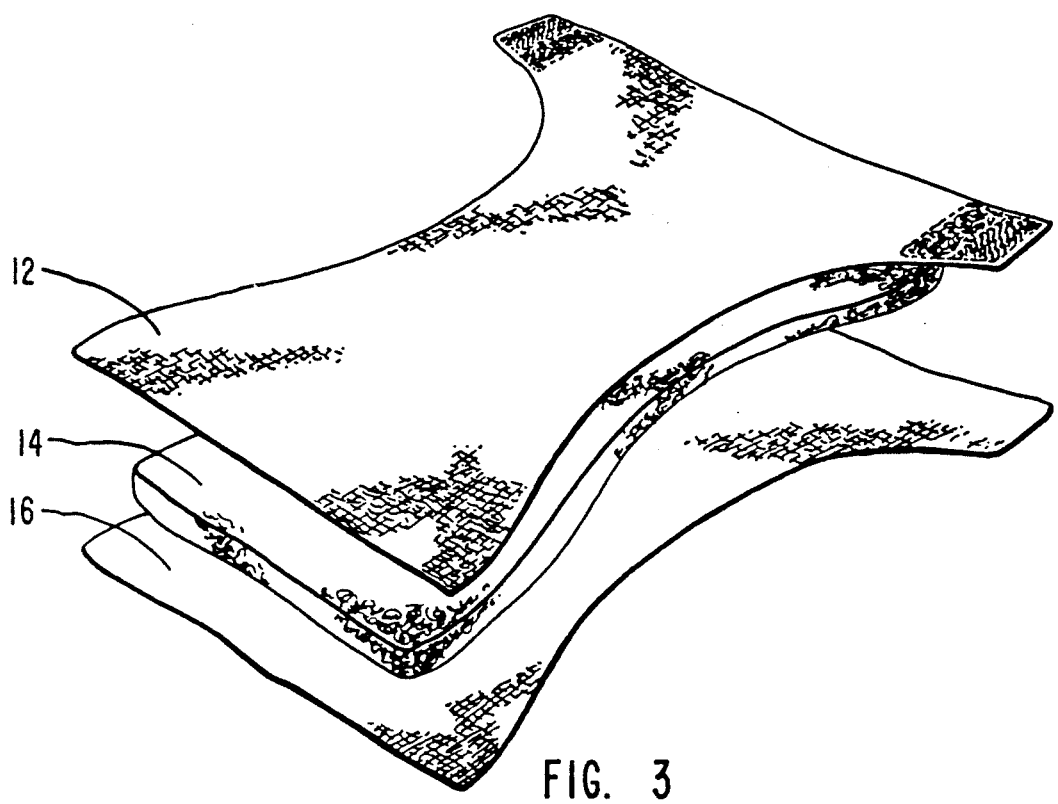
FIG. 3 is an exploded cross-sectional view of the present invention shown in FIG. 1.

FIG. 3 is a detailed illustration of front, middle, and back panels 12, 14, and 16, respectively, placed in relation to one another. According to one embodiment of the present invention, a reusable, multi-layered diaper is disclosed comprising a front panel 12 contacting a body, front panel 12 being a polyester wicking fabric. Preferably, front panel 12 is comprised of a fabric comprising COOL MAX®. COOL MAX® is a trademarked fabric distributed by the DuPont Corporation which is made of polyester.

The special four-channel fiber used in COOL MAX® fabrics features a unique structure with twenty percent more surface area than ordinary fibers. This special shape allows fabrics comprising COOL MAX® to transport moisture away from the skin and evaporate without absorbing liquids in the fiber itself. Compared to COOL MAX®, nylon absorbs more than eight times more liquid, and cotton and silk absorb more than fourteen times more liquid. In addition, COOL MAX® will not mildew or retain odors, resists stains and shrinking, and stays soft and flexible.

Although a fabric comprising COOL MAX® is the preferred fabric employed in the present invention as front panel 12, the present invention is not limited as such. Other materials similar to COOL MAX® may also be employed in front panel 12. Such other materials would transport moisture away from the skin and evaporate without any significant amount of the absorbing liquid in the materials itself.

Front panel 12 may also include soft substantially non-allergenic materials, such as cotton, polyester, nylon, and the like. Use of such materials would help to prevent allergic reactions to front panel 12.

The fabric marketed under the trademark of COOL MAX® typically can be purchased in a sheet, having weight in the range from about 5 to about 9 ½ ounces. A single sheet of fabric comprising COOL MAX®, or a plurality of sheets of fabric comprising COOL MAX®, may comprise front panel 12. Diaper 10 will eventually comprise a front panel 12, preferably employing in the range from about 6 to about 8 ounces of COOL MAX®.

The reusable, multi-layered diaper also comprises at least one middle panel 14 associated with front panel 12, at least one middle panel 14 being significantly absorbent. Preferably, at least one middle panel 14 is characterized by the presence of viscose fibers to increase the absorbency of at least one middle panel 14. In the most preferable embodiment of the present invention, at least one middle panel 14 is comprised of a fabric comprising VISCOSE® which is distributed under the fabric marketed and distributed by HUDCO located in Hayward, Calif.

VISCOSE® is 100 percent viscose rayon, which means cellulose has been treated with a solution of sodium hydroxide and carbon disulfide to make rayon threads and fabrics. This unique material is made up of fibers from the cellulose family so VISCOSE® is essentially a natural fabric. VISCOSE® is soft and drapes naturally after using. It becomes softer with use and improves with age.

VISCOSE® is also highly absorbent. Viscose filaments are woven into a felt-like fabric about ⅛ inch thick. Thousands of filaments form tiny air-cells that trap water droplets. In the present invention, at least one middle panel 14 comprises two layers of rectangularly-shaped fabric comprising VISCOSE®.

The fabric marketed under the trademark of VISCOSE® typically can be purchased in a sheet, and has a thickness in the range from about ⅛" to about ⅜". A single sheet of fabric comprising VISCOSE®, or a plurality of sheets of fabric comprising VISCOSE®, may comprise middle panel 14. Diaper 10 will eventually comprise a middle panel 14 being in the range from about ⅛" to about ⅜" thick, which would include about 1 to 3 layers of the fabric comprising VISCOSE® fibers. Preferably, middle panel 14 will be in the range from about ⅛" to about ⅜" thick, which would include about 1 to 3 layers of the VISCOSE® fibers.

In one embodiment, two layers of VISCOSE® of about 2/8" thickness each comprising middle panel 14 absorbs an amount of liquid in the range from about five to fifteen times the amount of the weight of middle panel 14. Preferably, middle panel 14 absorbs an amount of liquid in the range from about eight to twelve times the amount of the weight of middle panel 14. Most preferably, middle panel 14 absorbs about ten times its weight in liquid. Once the fabric is saturated, up to 92 percent of the water can easily be wrung out.

Although fabrics comprising VISCOSE® are the preferred fabrics employed in the present invention as at least one middle panel 14, the present invention is not limited as such. Other materials similar to the fabrics comprising VISCOSE® containing viscose fibers may also be employed in at least one middle panel 14. Such other materials would be highly absorbent to draw large amounts of liquids away from an infant's body.

In one embodiment of the present invention, middle panel 14 of reusable, multi-layered diaper 10 is comprised of a plurality of layers. Preferably, middle panel 14 is comprised of five layers. This plurality of layers can be comprised of fabrics comprising VISCOSE®, as previously discussed, or of any of a number of additional materials having the following characteristics: absorbent, quick-drying, avoids retention of odors.

Preferably, middle panel 14 is further comprised of at least one cotton-containing layer 18. Natural 100 percent cotton is one of the least allergenic materials known to man. Coincidentally, it is also a moisture absorbent material. Additionally, it is a highly gas pervious or breathable material. Finally, it offers a minimum bulk for its high moisture absorbency.

Figure 4:
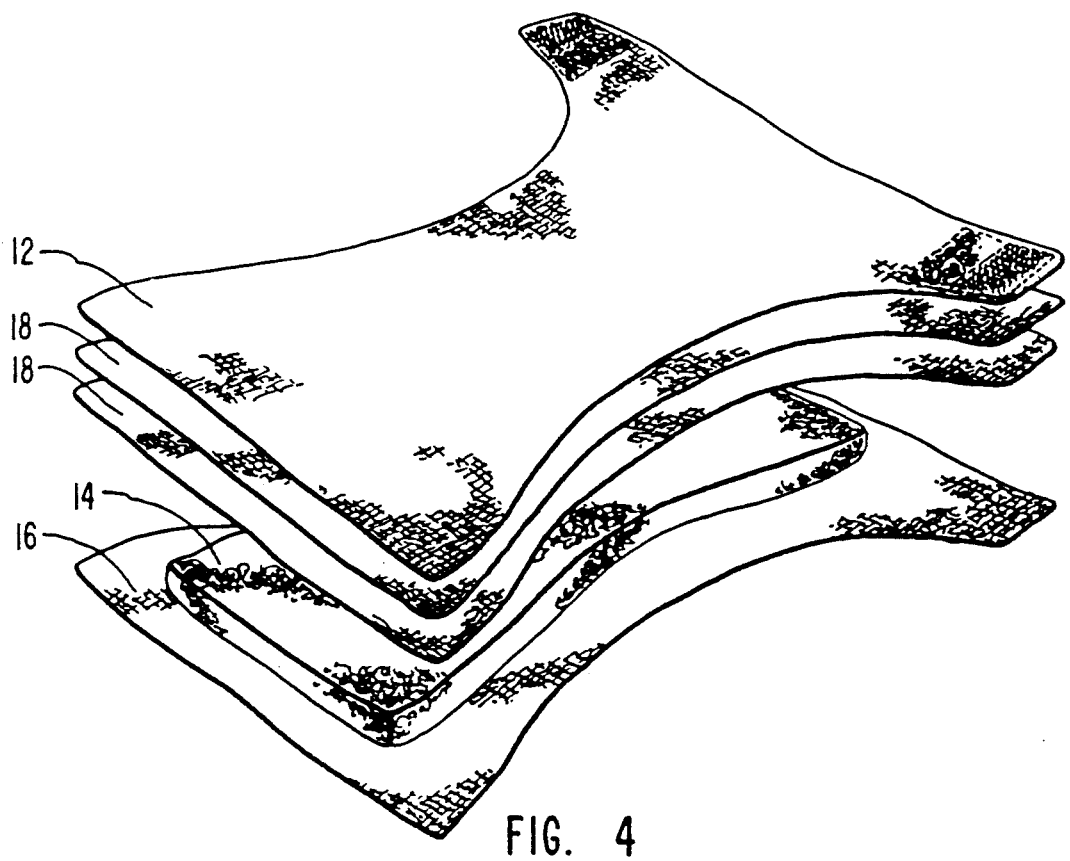
FIG. 4 is an exploded cross-sectional view of an additional embodiment of the present invention.

Because of these advantages presented by the use of cotton, a plurality of cotton layers 18 are employed in middle panel 14. Preferably, middle panel 14 is comprised of a layer of fabric comprising VISCOSE®, the layer of fabric comprising VISCOSE® having at least one cotton-containing layer 18 on one side of the layer of fabric comprising VISCOSE®. As shown in FIG. 4, two layers of 100 percent cotton are placed between the layer of fabric comprising VISCOSE® and the layer of fabric comprising COOL MAX® (alternatively, the two layers of 100 percent cotton 18 could be placed between the layer of fabric comprising VISCOSE® and back panel 16).

Figure 5:
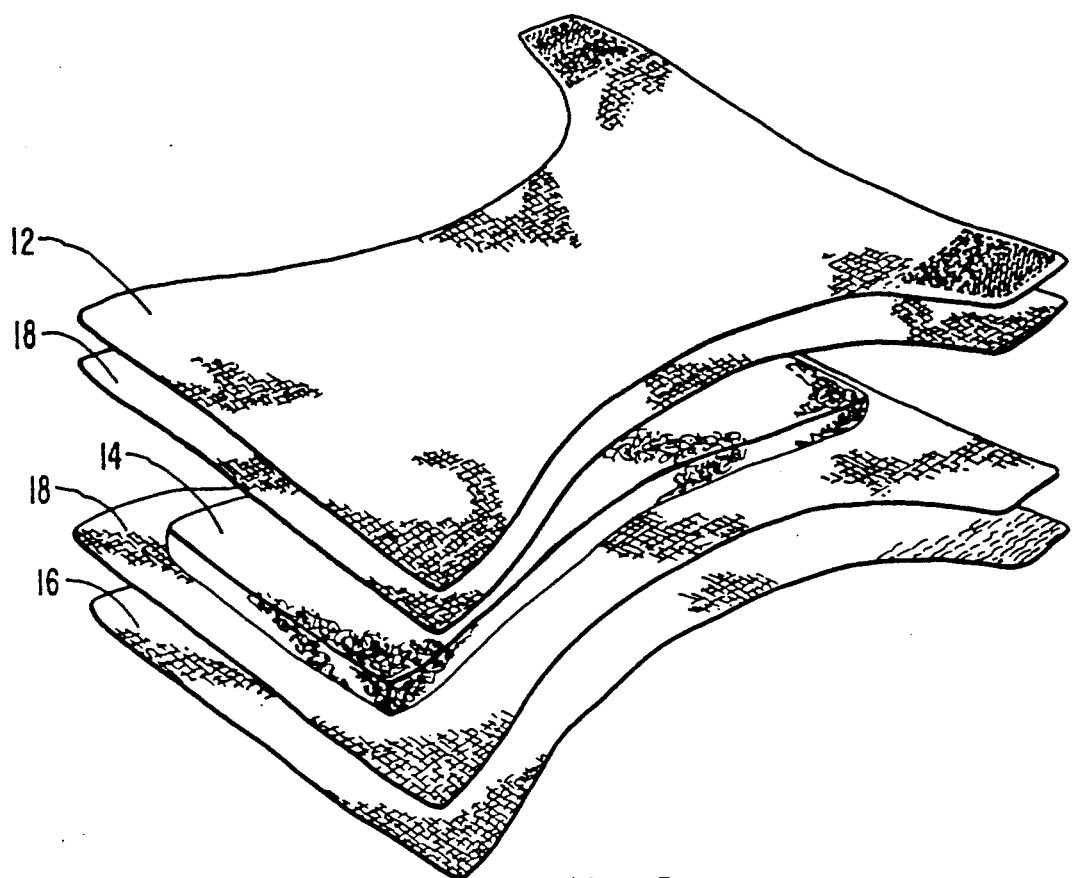
FIG. 5 is an exploded cross-sectional view of an additional embodiment of the present invention.

In another embodiment to the present invention, it has been found preferable that the at least one cotton-containing layer 18 is sandwiched about the layer containing viscose fibers. Most preferably, middle panel 14 is comprised of a layer of fabric comprising VISCOSE®, the layer of fabric comprising VISCOSE® having at least one cotton-containing layer 18 on both sides of the layer of fabric comprising VISCOSE®. As shown in FIG. 5, one layer of 100 percent cotton is placed between the layer of fabric comprising VIS- COSE® and the layer of fabric comprising COOL MAX®, and another layer of 100 percent cotton is placed between the layer of fabric comprising VISCOSE® and the layer of nylon. It is preferable to sandwich the cotton layer about the layer of fabric comprising VISCOSE® because the cotton helps spread moisture over the entire viscose layers, preventing pooling of moisture. The cotton layers are the same size and shape of the fabrics comprising COOL MAX® and the outer shell. The cotton gives body and helps the diaper retain its shape.

It is important to note that the number of cotton-containing layers 18 employed in the present invention is not critical. Any number of layers, of varying degrees of thickness, could be employed with diaper 10. It becomes more or less a matter of choice to different individuals with regard to the amount of cotton-containing layers employed, and the benefits offered by the absorbency and cushioning provided by the cotton-containing layers (diapers configured to a boy or girl may require additional padding in appropriate areas). Generally, about 1 to 4 cotton-containing layers are placed in diaper 10.

The reusable, multi-layered diaper is also comprised of back panel 16 associated with at least one middle panel 14, back panel 16 is impermeable to liquids such that diaper 10 is waterproof. Back panel 16 is preferably comprised of water-proof nylon. Nylon is preferred because it keeps its shape, launders easily, dries quickly, resists stains, and is non-irritating to most people. However, the present invention is not limited as such and other materials impermeable to liquids may be employed.

In the most preferred embodiment of the present invention, nylon back panel 16 is urethane-treated. The nylon is dipped into urethane and dried for about 72 hours before it can be used. The urethane fills in the needle holes created when the fabric is woven. Regular nylon is not waterproof but is water repellent. When you touch nylon that is water repellent, moisture penetrates the material, thus causing wetness. Nylon that has been treated with urethane does not allow the penetration of any moisture.

The nylon taffeta fabric typically can be purchased in a sheet having a range from about 68 to about 86 threads per inch. A single sheet of nylon, or a plurality of sheets of nylon, may comprise back panel 16. Diaper 10 will eventually comprise a back panel 16. Preferably, back panel 16 will be nylon taffeta of about 80–90 threads per inch.

According to one aspect of the present invention, front and back panels 12 and 16 are joined together by connecting means. As shown in FIG. 1, the front and back panels 12 and 16 are stitched together in a quilting pattern, as shown by dotted lines to generally immobilize at least one middle panel 14 to maintain their position and thickness after repeated washing and drying cycles. Alternatively, front and back panels 12 and 16 can be joined together by other connecting means known to those skilled in the art, such as adhesives.

The quilting pattern used to join front and back panels 12 and 16 may provide some decorative features to back panel 16. Alternatively, a decorative back panel 16 of suitably colored or characteristic fabric may be provided to cover back panel 16 and becomes the outer and visible surface of diaper 10 as worn. Some other type of decorating means known to those skilled in the art may also be used to adorn or garnish back panel 16.

Diaper 10 is preferably "T"-shaped or possibly hour glass-shaped. Nevertheless, the present invention is not limited to this type of shape. What is most important in terms of shape is that diaper 10 be configured such that diaper 10 may be placed about the waist area of an individual. Thus, any shape known to those skilled in the art may be used in the present invention.

As illustrated in FIG. 1, the preferred embodiment of the present invention comprises diaper 10 as "T"-shaped. Diaper 10 is comprised of opposingly positioned front waist area 20 and back waist area 22 formed in communication with a front crotch area 24 and a back crotch area 26. Front crotch area 24 and back crotch area 26 are provided intermediate of front waist area 20 and back waist area 22. Diaper 10 at this point has a generally rectangular effect due to the presence of the waist areas 20 and 22 and the crotch areas 24 and 26.

Positioned laterally of crotch areas 24 and 26 and intermediate of waist areas 20 and 22 of diaper 10 are leg areas 32. Leg areas 32 are concavely curved and leg conforming. Once diaper 10 is fitted to an infant, the curved nature of leg areas 32 conforms about, in a substantially circular or oval fashion, about a leg.

As shown in FIG. 2, the waist areas are preferably provided with elastic ribbons 40, interposed between front and back panels 12 and 16, to permit the waist areas to expand or retract to accommodate the size of the infant and to provide a snug fit about the infant's waist. The perimeter of leg areas 32 are provided with relatively thin elastic ribbons 40 attached to the margins of leg areas 32 to permit leg areas 32 to expand or retract to accommodate the size of the infant and to provide a snug fit about the infant's legs to prevent leakage.

As illustrated in FIG. 1, in the preferred embodiment of the present invention, diaper 10 is further comprised of winged tabs 42. Winged tabs 42 are formed at the corners 44 of back waist area 22 extending outwardly. Winged tabs 42 are configured such that winged tabs 42 may be pressed against and secured to an area of front waist area 20, preferably corners 46 of front waist area 20.

In one embodiment of the present invention, reusable, multi-layered diaper 10 comprises a fastening surface 48 in association with winged tabs 42. Fastening surface 48 is attached to the front side 50 of winged tabs 42 to connect front and back waist areas 20 and 22. Thus, when winged tabs 42 are pressed against the front waist area 20, front and back waist areas 20 and 22 are joined and diaper 10 is fitted to an infant.

Preferably, fastening surface 48 is a loop and hook device, such as that commonly sold under the trade name VELCRO ®. The Velcro fastener cooperates with a receiving surface 54 on front waist area 20.

Receiving surface 54 on front waist area 20 may also be comprised of Velcro fasteners. The velcro fasteners are preferably attached as a two inch strip on front waist area 20. Nevertheless, velcro fasteners may be various sizes and lengths known to those skilled in the art.

Whereas the use of VELCRO ® is preferred, it should be understood that other types of fastening devices are known in the art. Fastening surface 48 may be tape or other adhesive. Fastening devices would join front and back waist areas 20 and 22 about the waist of an infant.

Although it is not required, corners 46 of front waist area 20 may extend outwardly to aid in the attachment of back waist area 22 to front waist area 20. As shown in FIG. 1, corners 46 are only slightly outwardly extending, thus continuing to provide diaper 10 with a "T"-shaped appearance. It could be understood, however, that corners 46 could be outwardly extended to such a degree that diaper 10 would have the appearance of an hourglass-shape.

Figure 6:
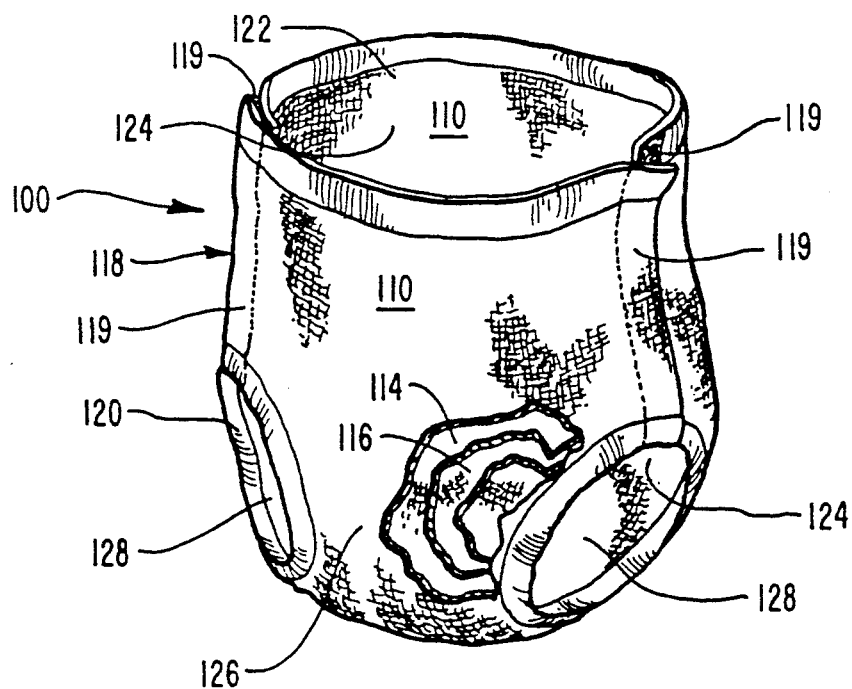
FIG. 6 is a perspective view of another embodiment of the present invention where the reusable, multi-layered, moisture retention features are present in a training pant for toddlers.

In another embodiment of the present invention, the reusable, multi-layered, moisture retention features of the present invention are incorporated into a pull-up training pant 100. A pull-up training pant differs from a diaper by the age of the child for which it is targeted; a diaper is used with newborns whereas a pull-up training pant is used for toddlers. A pull-up training pant 100 having the reusable, multi-layered, moisture retention features of the present invention is illustrated in FIG. 6.

The training pant 100 preferably uses two layers of 100% cotton knit 110 (one for the outside layer and one for the inside layer). The second layer starting from the outside in is of waterproof nylon taffeta 116. The third layer is rayon viscose 114 and the inside layer is of cotton 110. The sides 111 are left open in the sewing process and snaps, Velcro fasteners, or other closing devices, or a combination of the above, (Velcro fasteners are illustrated at 119) will be used on the sides to allow the training pant 100 to close. Elastic 120 is inserted at the waist 122, back 124 and front 126, and also around each leg opening 128. Cotton ribbing is attached to form a leg band and a waist band.

Although the preferred construction of the training pant 100 has been discussed, it should be understood that training pant 100 is not limited as such. Training pant 100 may incorporate the teachings previously discussed with regard to diaper 10. Training pant 100 may employ the fabrics and use the principles of construction which have been thoroughly explained in regard to diaper 10.

EXAMPLES

Example 1

A diaper was prepared according to the principles presented in the disclosed present invention. A front sheet of the fabric comprising COOL MAX®, purchased from Summit Knitting Mills, Inc., was cut into a "T"-shape. The sheet was configured to provide for winged tabs positioned at what would be the corners of the front and back waist areas of the diaper.

Next, a middle sheet of the fabric comprising VISCOSE® being ¼" thick was cut into a "T"-shape which corresponded the pre-cut fabric comprising COOL MAX® being 6–8 ounces. The fabric comprising VISCOSE® was positioned adjacent to the fabric comprising COOL MAX®.

Then, an outer sheet of nylon fabric (86 threads per inch) was cut into a "T"-shape which corresponded to the pre-cut VISCOSE® and COOL MAX® fabrics. After the nylon taffeta fabric was positioned adjacent to the VISCOSE® fabric, the nylon taffeta fabric was stitched to the COOL MAX® fabric. The stitching positioned the intermediate layer of fabric comprising VISCOSE® such that the intermediate layer would not move about. Preferably, the intermediate layer would not move. If the fabric comprising VISCOSE® was not stitched on both sides it would have twisted in the laundering process. As shown in FIG. 2, the leg areas were provided with elastic ribbons interposed between front and back panels 12 and 16 to permit leg areas to expand or retract to accommodate the infant's leg and provide a snug, leakproof fit.

Finally, Velcro fastening surfaces were placed on the winged tabs found on the back waist area, and on the front waist area. The use of the Velcro fasteners allowed the front and back waist area to be joined. Thus, the diaper could be configured about an infants body to contain urine and fecal wastes.

The construction of the layers according to the foregoing steps provided a diaper which had approximately 10 times the absorbency over prior known diapers. The diapers wicked away moisture from an infant's bottom unlike other known diapers, thus preventing diaper rash. Such a construction was also economically sound because the materials comprising the layers could be washed and reused indefinitely and, therefore, the diaper could be reused and not disposed of.

Example 2

A diaper was prepared according to the steps of Example 1. The diaper of Example 2, however, further comprised two layers of cotton. Use of the cotton layers further enhanced the absorptive nature of the diaper, and provided cushioning to the infant in a seated position. The cotton layers were positioned such that one cotton layer was positioned between the VISCOSE® and nylon-comprising layers, and the other cotton layer was positioned between the VISCOSE® and COOL MAX® layers.

Example 2 is important to illustrate that additional layers of fabrics, previously known in the diaper art, may be employed with the diaper of the present invention. These additional layers may provide increased absorbent, wicking, or cushioning benefits to the diaper of Example 1.

Example 3

A training pant was prepared according to the principles presented in the disclosed present invention. Several pieces of fabric were cut into an hourglass shape. The fabric layers were placed next to each other, the types of materials corresponding to the following order starting with the inside layer: (1) cotton knit; (2) rayon viscose; (3) nylon taffeta; and (4) cotton knit.

After the fabric layers were positioned, the cotton knit layers were stitched to one another. The stitching positioned the intermediate rayon viscose and nylon taffeta layers such that the intermediate layers would not move about. The stitching was made in a decorative pattern.

During the sewing process, the sides were left open such that the training pants could be placed on a toddler without the toddler's feet having to have been placed through two leg openings. To secure the training pant to the toddler's waist, Velcro fasteners were incorporated along the sides of the training pant. The Velcro fasteners allowed the training pant to close about the infant's waist after the training pant was placed about the toddler.

The leg areas were provided with elastic ribbons interposed between the front and back layers to permit the leg areas to expand and retract to accommodate the infant's leg and provide a snug, leakproof fit. Cotton ribbing was attached to form a leg band and a waist band.

Example 3 is important to illustrate that the teachings of the present invention may be applied to diaper-related constructions such as a training pant. The training pant has approximately ten times the absorbency over prior known training pants. The training pants can wick away moisture from an infant's bottom unlike other known training pants, thus preventing diaper rash. The construction is economically sound because the materials comprising the layers can be washed and reused indefinitely and, therefore, the diaper can be reused and not disposed of.

Hypothetical 4

A diaper is prepared according to the procedure outlined in Example 1, wherein one layer of viscose and one layer of flannel was used and the area around the navel was cut out. This results in a diaper which can be characterized as an all-in-one diaper for newborns. This result is important to show that the diaper is not irritating to the umbilical cord of an infant while still absorbent and not bulky.

Hypothetical 5

A diaper is prepared according to the procedure outlined in Example 1, wherein one extra layer of viscose was sewn in the crotch area only. This results in a diaper which can be characterized by a diaper for girls. This result is important to show a diaper that is designed to be ultra-absorbent in the crotch area where baby girls may need extra protection.

Hypothetical 6

A diaper is prepared according to the procedure outlined in Example 1, wherein one extra layer of viscose was sewn in the front area only. This results in a diaper which can be characterized as a diaper for boys. This result is important to show a diaper that is designed to be ultra-absorbent in the front area where baby boys may need extra protection.

SUMMARY

From the foregoing, it will be appreciated that the present invention provides an apparatus and methods for a diaper which is reusable and provides an ecologically sensible alternative to disposable diapers. Additionally, the present invention provides an apparatus and methods for a diaper which will absorb many times its weight in liquids.

The present invention also provides apparatus and methods for a diaper which will absorb many times its weight while holding rash-causing moisture away from a baby's skin. The present invention further provides an apparatus and methods for a diaper containing a layer of material that exceeds moisture from flowing back to a baby's skin.

The present invention may be embodied in other specific forms, such as training pants and adult diapers, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A reusable, multi-layered diaper to be worn about a body of an individual, the diaper comprising:
    (a) a first layer for contacting the body of the individual, the first layer being a polyester wicking fabric to draw moisture away from the body of the individual;
    (b) a middle panel comprising a plurality of layers secured beneath the first layer, at least one of the plurality of layers being absorbent and characterized by a presence of viscose rayon fibers and two of the plurality of layers being comprised of cotton, the two cotton-containing layers being sandwiched about the at least one absorbent layer of fabric containing viscose rayon fibers; and
    (c) an outer layer secured beneath the middle panel to the first layer, the outer layer being impermeable to liquids such that the diaper is waterproof.

2. A reusable, multi-layered diaper to be worn about a body of an individual, the diaper comprising:
    (a) a first layer for contacting the body of its individual, the first layer being a polyester wicking fabric to draw moisture away from the body of the individual;
    (b) a middle panel comprising a plurality of layers secured beneath the first layer, at least one of the plurality of layers being absorbent and characterized by a presence of viscose rayon fibers and at least one of the plurality of layers being comprised of cotton; and
    (c) an outer layer secured beneath the middle panel to the first layer, the outer layer being impermeable to liquids such that the diaper is waterproof, and wherein the cotton containing layer of the plurality of layers in the middle panel is disposed between the absorbent layer of fabric containing viscose rayon fibers of the plurality of layers in the middle panel and the outer layer.

3. A reusable, multi-layered diaper as defined in claim 2, wherein the diaper further comprises additional layers of a polyester wicking fabric.

4. A reusable, multi-layered diaper as defined in claim 2, wherein the diaper further comprises additional absorbent middle layer containing viscose rayon fibers.

5. A reusable, multi-layered diaper as defined in claim 2, wherein the outer layer is comprised of nylon containing fabrics.

6. A reusable, multi-layered diaper as defined in claim 2, wherein the middle panel comprises three layers.

7. A reusable, multi-layered diaper as defined in claim 2, wherein the middle panel comprises five layers.

8. A reusable, multi-layered diaper as defined in claim 2, wherein the diaper comprises two cotton containing middle layers.

9. A reusable, multi-layered diaper as defined in claim 2, wherein a cotton-containing layer is disposed between the layer containing viscose rayon fibers and the inner layer.

10. A reusable, multi-layered diaper as defined in claim 2, wherein the at least one absorbent layer absorbs an amount of liquid, in a range from about five to fifteen times an amount of weight of the at least one absorbent layer.

11. A reusable, multi-layered diaper as defined in claim 2, wherein the at least one absorbent layer absorbs an amount of liquid in a range from about eight to twelve times, an amount of weight of the at least one absorbent layer.

12. A reusable, multi-layered diaper as defined in claim 2, further comprising velcro fasteners attached to the reusable, multi-layered diaper.

13. A reusable, multi-layered diaper as defined in claim 2, wherein the reusable, multi-layered diaper is T-shaped to conform to a baby's waist and legs.

14. A reusable, multi-layered diaper to be worn about a body of an individual, the diaper comprising:
   (a) a first layer for contacting the body of the individual, the first layer being comprised of a polyester wicking fabric;
   (b) at least one middle layer secured beneath the first layer, the at least one middle layer characterized by a presence of viscose rayon fibers to increase absorbency of the at least one middle layer, the at least one middle layer further comprising cotton containing layer; and
   (c) an outer layer secured beneath the at least one middle layer to the first layer, the outer layer being comprised of nylon such that the diaper is impermeable to liquids and water-proof, and wherein the cotton containing layers are disposed between the at least one middle layer comprised of viscose rayon fibers and the outer layer.

15. A reusable, multi-layered diaper as defined in claim 14, wherein the cotton containing layers are sandwiched about the at least one middle layer containing viscose rayon fibers.

16. A reusable, multi-layered diaper as defined in claim 14, wherein the first layer of polyester wicking fabric has a weight in a range of from about six to about eight ounces.

17. A reusable, multi-layered diaper as defined in claim 14, wherein the at least one middle layer containing viscose rayon fibers has a thickness in a range of from about one-eighth inch to about three-eighth inches thick.

18. A reusable, multi-layered diaper as defined in claim 14, wherein the diaper comprises an additional absorbent layer in a front area of said diaper so as to be configured for a boy.

19. A reusable, multi-layered diaper as defined in claim 14, wherein the diaper comprises an additional absorbent layer in a crotch of said diaper so as to be configured for a girl.

20. A reusable, multi-layered training pant to be worn about a body of an individual, the training pant comprising:
   (a) a first layer for contacting the body of the individual comprised of a polyester wicking fabric;
   (b) a second layer secured beneath the first layer, the second layer characterized by a presence of fabric containing viscose rayon fibers to increase the absorbency of the second layer;
   (c) a third layer secured beneath the second layer to the first layer, the third layer comprised of nylon such that the training pant is impermeable to liquids and water-proof; and
   (d) an outer layer secured beneath the third layer, the outer layer comprised of a cotton knit fabric.

21. A reusable, multi-layered training pant to be worn about a body of an individual, the training pant comprising:
   (a) a first layer for contacting the body of the individual comprised of a polyester wicking fabric;
   (b) a second layer secured beneath the first layer, the second layer characterized by a presence of fabric containing viscose rayon fibers to increase absorbency of the second layer;
   (c) a third layer secured beneath the second layer to the first layer, the third layer comprised of nylon such that the training pant is impermeable to liquids and water-proof;
   (d) an outer layer secured beneath the third layer, the outer layer comprised of a cotton knit fabric; and
   (e) at least one additional cotton containing layer disposed between the first and third layers.

22. A reusable, multi-layered training pant as defined in claim 21, wherein the cotton-containing layers are sandwiched about the second layer.

23. A reusable, multi-layered training pant as defined in claim 21, wherein at least one additional cotton-containing layer is disposed between the second layer and the first layer.

24. A reusable, multi-layered training pant as defined in claim 21, wherein at least one additional cotton-containing layer is disposed between the second layer and the third layer.

25. A reusable, multi-layered diaper to be worn about a body of an individual, the diaper comprising:
   (a) a first layer for contacting the body of the individual, the first layer being comprised of a multi-channeled polyester wicking fiber to transport and evaporate fluid without absorbing fluids in the fiber;
   (b) at least one middle layer secured beneath the first layer, the at least one middle layer characterized by a presence of viscose rayon fibers to increase absorbency of the at least one middle layer, the at least one middle layer capable of absorbing an amount of fluid in the range from about five to fifteen times the weight of the at least one middle layer;
   (c) an outer layer secured beneath the at least one middle layer to the first layer, the outer layer being comprised of nylon such that the diaper is impermeable to fluids; and
   (d) at least one additional cotton containing layer between the inner and outer layers, the at least one additional cotton containing layer being disposed between the at least one middle layer containing viscose rayon fibers and the outer layer.

* * * * *